US008187190B2

(12) United States Patent
Dala-Krishna

(10) Patent No.: US 8,187,190 B2
(45) Date of Patent: May 29, 2012

(54) METHOD AND SYSTEM FOR CONFIGURATION OF A PACEMAKER AND FOR PLACEMENT OF PACEMAKER ELECTRODES

(75) Inventor: Praveen Dala-Krishna, Sicklerville, NJ (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1019 days.

(21) Appl. No.: 11/610,924

(22) Filed: Dec. 14, 2006

(65) Prior Publication Data
US 2008/0146928 A1 Jun. 19, 2008

(51) Int. Cl.
A61B 8/00 (2006.01)
(52) U.S. Cl. .................. 600/443; 600/437; 600/450
(58) Field of Classification Search .............. 600/407, 600/437, 443, 450, 454, 462, 467, 468
See application file for complete search history.

(56) References Cited

U.S. PATENT DOCUMENTS

| | | | |
|---|---|---|---|
| 4,161,121 A | 7/1979 | Zitelli et al. |
| 4,241,610 A | 12/1980 | Anderson |
| 4,462,408 A | 7/1984 | Silverstein et al. |
| 4,519,260 A | 5/1985 | Fu et al. |
| 4,576,177 A | 3/1986 | Webster, Jr. |
| 4,605,009 A | 8/1986 | Pourcelot et al. |
| 4,841,977 A | 6/1989 | Griffith et al. |
| 4,890,268 A | 12/1989 | Smith et al. |
| 4,917,097 A | 4/1990 | Proudian et al. |
| 4,951,677 A | 8/1990 | Crowley et al. |
| 5,002,059 A | 3/1991 | Crowley et al. |
| 5,090,956 A | 2/1992 | McCoy |
| 5,105,819 A | 4/1992 | Wollschlager et al. |
| 5,152,294 A | 10/1992 | Mochizuki et al. |
| 5,158,087 A | 10/1992 | Gatzke |
| 5,170,793 A | 12/1992 | Takano et al. |
| 5,195,968 A | 3/1993 | Lundquist et al. |
| 5,211,169 A | 5/1993 | Freeland |
| 5,254,088 A | 10/1993 | Lundquist et al. |
| 5,279,559 A | 1/1994 | Barr |
| 5,287,753 A | 2/1994 | Routh et al. |
| 5,307,816 A | 5/1994 | Hashimoto et al. |
| 5,309,914 A | 5/1994 | Iinuma |
| 5,325,860 A | 7/1994 | Seward et al. |

(Continued)

OTHER PUBLICATIONS

Packer, D. et al, "Intracardiac Phased-Array Imaging: Methods and Initial Clinical Experience with High Resolution, Under Blood Visualization," Journal of the American College of Cardiology, vol. 39, No. 3, Feb. 2002.

(Continued)

*Primary Examiner* — Tse Chen
*Assistant Examiner* — Rochelle Reardon
(74) *Attorney, Agent, or Firm* — The Marbury Law Group, PLLC

(57) ABSTRACT

Ultrasound imaging methods and systems for assisting a clinician in configuring the operation of a pacemaker and for determining an optimal site for the pacemaker electrode are presented. The methods and systems provide a toolbox for analyzing and optimizing the effectiveness of the pacemaker and proposed electrode sites. The method includes a function which evaluates one or more electrode sites and pacemaker configurations. The function may be based, for example, on the activation voltage of the pacemaker, on an estimate of the volume of blood ejected from the heart and/or on the cardiac dysynchrony. The ejection volume and the dysynchrony may be estimated using an imaging cardiac catheter ultrasound transducer array and ultrasound unit.

21 Claims, 9 Drawing Sheets

U.S. PATENT DOCUMENTS

| | | | |
|---|---|---|---|
| 5,336,182 A | 8/1994 | Lundquist et al. | |
| 5,345,938 A | 9/1994 | Nishiki et al. | |
| 5,345,940 A | 9/1994 | Seward et al. | |
| 5,357,550 A | 10/1994 | Asahina et al. | |
| 5,358,478 A | 10/1994 | Thompson et al. | |
| 5,364,351 A | 11/1994 | Heinzelman et al. | |
| 5,372,138 A | 12/1994 | Crowley et al. | |
| 5,385,148 A | 1/1995 | Lesh et al. | |
| 5,395,327 A | 3/1995 | Lundquist et al. | |
| 5,438,997 A | 8/1995 | Sieben et al. | |
| 5,456,258 A | 10/1995 | Kondo et al. | |
| 5,456,664 A | 10/1995 | Heinzelman et al. | |
| 5,470,350 A | 11/1995 | Buchholtz et al. | |
| 5,499,630 A | 3/1996 | Hiki et al. | |
| 5,515,853 A | 5/1996 | Smith et al. | |
| 5,515,856 A | 5/1996 | Olstad et al. | |
| 5,531,686 A | 7/1996 | Lundquist et al. | |
| 5,560,362 A | 10/1996 | Sliwa, Jr. et al. | |
| 5,588,432 A | 12/1996 | Crowley | |
| 5,622,174 A | 4/1997 | Yamazaki | |
| 5,634,465 A | 6/1997 | Schmiesing et al. | |
| 5,662,116 A | 9/1997 | Kondo et al. | |
| 5,697,965 A | 12/1997 | Griffin, III | |
| 5,699,805 A | 12/1997 | Seward et al. | |
| 5,701,897 A | 12/1997 | Sano | |
| 5,704,361 A | 1/1998 | Seward et al. | |
| 5,713,363 A | 2/1998 | Seward et al. | |
| 5,715,817 A | 2/1998 | Stevens-Wright et al. | |
| 5,722,403 A | 3/1998 | McGee et al. | |
| 5,749,364 A | 5/1998 | Sliwa, Jr. et al. | |
| 5,788,636 A | 8/1998 | Curley | |
| 5,795,299 A | 8/1998 | Eaton et al. | |
| 5,797,396 A * | 8/1998 | Geiser et al. | 600/407 |
| 5,797,848 A | 8/1998 | Marian et al. | |
| 5,800,356 A | 9/1998 | Criton et al. | |
| 5,807,324 A | 9/1998 | Griffin, III | |
| 5,833,624 A | 11/1998 | Rom et al. | |
| 5,846,205 A | 12/1998 | Curley et al. | |
| 5,888,577 A | 3/1999 | Griffin, III et al. | |
| 5,891,088 A | 4/1999 | Thompson et al. | |
| 5,906,579 A | 5/1999 | Vander Salm et al. | |
| 5,916,168 A | 6/1999 | Pedersen et al. | |
| 5,921,978 A | 7/1999 | Thompson et al. | |
| 5,928,276 A | 7/1999 | Griffin, III et al. | |
| 5,931,863 A | 8/1999 | Griffin, III et al. | |
| 5,935,102 A | 8/1999 | Bowden et al. | |
| 5,938,616 A | 8/1999 | Eaton et al. | |
| 5,954,654 A | 9/1999 | Eaton et al. | |
| 6,013,072 A | 1/2000 | Winston et al. | |
| 6,033,378 A | 3/2000 | Lundquist et al. | |
| 6,039,693 A | 3/2000 | Seward et al. | |
| 6,085,117 A | 7/2000 | Griffin, III et al. | |
| 6,144,870 A | 11/2000 | Griffin, III | |
| 6,171,248 B1 | 1/2001 | Hossack et al. | |
| 6,173,205 B1 | 1/2001 | Griffin, III et al. | |
| 6,190,353 B1 | 2/2001 | Makower et al. | |
| 6,210,333 B1 | 4/2001 | Gardner et al. | |
| 6,224,556 B1 | 5/2001 | Schwartz et al. | |
| 6,228,028 B1 | 5/2001 | Klein et al. | |
| 6,228,032 B1 | 5/2001 | Eaton et al. | |
| 6,261,246 B1 | 7/2001 | Pantages et al. | |
| 6,285,898 B1 * | 9/2001 | Ben-Haim | 600/374 |
| 6,293,943 B1 | 9/2001 | Pansecu et al. | |
| 6,306,096 B1 | 10/2001 | Seward et al. | |
| 6,306,097 B1 | 10/2001 | Park et al. | |
| 6,310,828 B1 | 10/2001 | Mumm et al. | |
| 6,358,208 B1 | 3/2002 | Lang et al. | |
| 6,360,027 B1 | 3/2002 | Hossack et al. | |
| 6,368,275 B1 | 4/2002 | Sliwa et al. | |
| 6,385,489 B1 | 5/2002 | Griffin, III et al. | |
| 6,398,731 B1 | 6/2002 | Mumm et al. | |
| 6,423,002 B1 | 7/2002 | Hossack | |
| 6,440,488 B2 | 8/2002 | Griffin, III et al. | |
| 6,443,894 B1 | 9/2002 | Sumanaweera et al. | |
| 6,475,148 B1 | 11/2002 | Jackson et al. | |
| 6,475,149 B1 | 11/2002 | Sumanaweera | |
| 6,482,161 B1 | 11/2002 | Sumanaweera et al. | |
| 6,485,455 B1 | 11/2002 | Thompson et al. | |
| 6,491,633 B1 | 12/2002 | Krishnan et al. | |
| 6,503,202 B1 | 1/2003 | Hossack et al. | |
| 6,517,488 B1 | 2/2003 | Hossack | |
| 6,527,717 B1 | 3/2003 | Jackson et al. | |
| 6,527,718 B1 * | 3/2003 | Connor et al. | 600/439 |
| 6,532,378 B2 | 3/2003 | Saksena et al. | |
| 6,554,770 B1 | 4/2003 | Sumanaweera et al. | |
| 6,589,182 B1 | 7/2003 | Loftman et al. | |
| 6,605,043 B1 | 8/2003 | Dreschel et al. | |
| 6,607,488 B1 | 8/2003 | Jackson et al. | |
| 6,607,528 B1 | 8/2003 | Quick et al. | |
| 6,612,992 B1 | 9/2003 | Hossack et al. | |
| 6,645,147 B1 | 11/2003 | Jackson et al. | |
| 6,648,875 B2 | 11/2003 | Simpson et al. | |
| 6,709,396 B2 | 3/2004 | Flesch et al. | |
| 6,908,434 B1 | 6/2005 | Jenkins et al. | |
| 6,923,768 B2 | 8/2005 | Camus et al. | |
| 7,097,619 B2 | 8/2006 | Von Behren et al. | |
| 2003/0045796 A1 | 3/2003 | Friedman | |
| 2003/0158483 A1 | 8/2003 | Jackson et al. | |
| 2004/0097805 A1 | 5/2004 | Verard et al. | |
| 2004/0249282 A1 | 12/2004 | Olslad | |
| 2005/0203390 A1 | 9/2005 | Torp et al. | |
| 2005/0203395 A1 | 9/2005 | Sui et al. | |
| 2009/0131788 A1 | 5/2009 | Settlemier et al. | |

OTHER PUBLICATIONS

Ihlen, H. et al, "Determination of Cardiac Output by Doppler Echocardiography," British Heart Journal, 1984, 51: 54-60.

* cited by examiner

Fig. 3

| Site | Stimulation Voltage | EF | V-V Delay | Merit |
|---|---|---|---|---|
| B | 210 mV | 46% | 87 ms | 137 |
| A | 200 mV | 39% | 121 ms | 77 |
| C | 210 mV | 41% | 111 ms | 89 |
| C | 230 mV | 42% | 109 ms | 91 |
| * | 0 mV | 30% | 199 | 41 |

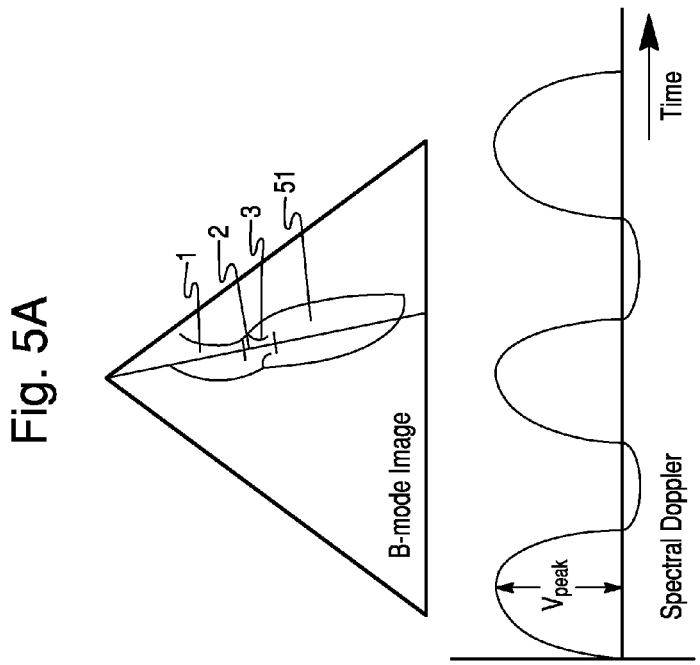
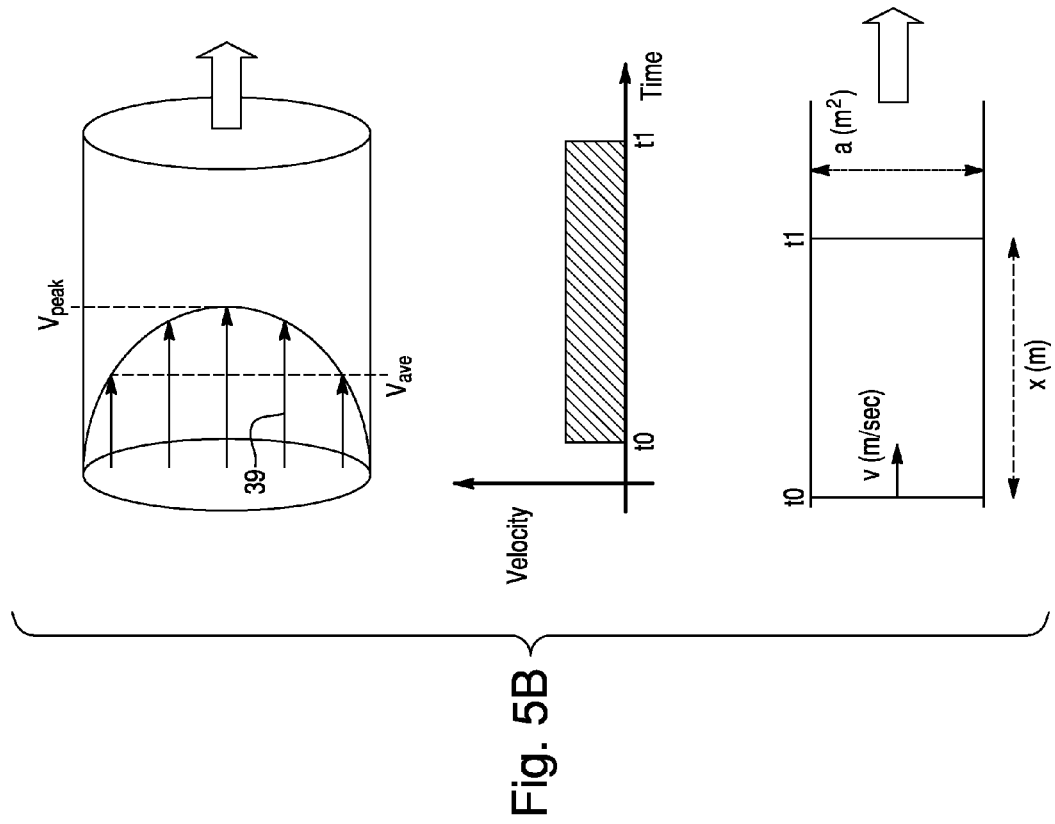
Fig. 5A
Fig. 5B

METHOD AND SYSTEM FOR CONFIGURATION OF A PACEMAKER AND FOR PLACEMENT OF PACEMAKER ELECTRODES

FIELD OF THE INVENTION

The present invention relates to techniques for assisting a clinician in determining a site for a cardiac pacemaker electrode and for determining a configuration for the pacemaker driving the electrode.

BACKGROUND OF THE INVENTION

Volumetric output of blood from the heart and/or circulatory system is of interest in various diagnostic and therapeutic procedures. Such measurements are of significant interest during evaluation or therapy to evaluate the extent of dysynchrony due to arrhythmia and subsequently to judge the effectiveness of any therapeutic procedures that are carried out on the cardiac muscle and conduction system Iwa et al., Eur. J. Cardithorac. Surg., 5, 191-197 (1991).

Ultrasound is the imaging modality of choice, especially in cardiology, since this modality offers real-time imaging capabilities of the moving heart. Further, advances through Doppler or speckle tracking techniques allow the physician to visualize as well as measure blood flow. Pulse wave and continuous wave Doppler have proven to be quite accurate, and an effective way of evaluating flow through various parts of the circulatory system, especially the heart. Tortoli et al., Ultrasound Med. Bio., 28, 249-257 (2002); Mohan et al., Pediatr. Cardiol. 23, 58-61 (2002); Ogawa et al., J. Vasc. Surg., 35, 527-531 (2002); Pislaru et al., J. Am. Coll. Cardiol., 38, 1748-1756 (2001).

Other technologies, including washout curves of contrast agents have been proposed to measure flow volume, especially to compensate for loss of signal quality due to imaging depth. Krishna et al., Ultrasound Med. Bio., 23, 453-459 (1997); Schrope et al., Ultrasound Med. Bio., 19, 567-579 (1993).

However, until recent advances in miniaturized ultrasonic transducers, physicians were limited to only certain angles of view, thus limiting the range and effectiveness of possible measurements. Further, given the depth of imaging required by such classical approaches, associated interrogation frequency limitations due to attenuation restricted the accuracy of measurement. Krishna et al., Phys. Med. Biol., 44, 681-694 (1999). With the recent introduction of catheter based transducers for imaging the heart from either the vena-cava or even from within the heart, such limitations on frequency of interrogation and angle of view are not applicable.

One specific need for this invention is for the permanent placement of cardiac pacing electrodes. Cardiac pacing has been around for many years, and essentially involves the placement of a permanent electrode in the right ventricle to quicken the pace of an otherwise slow heart. A new therapy has recently been introduced to the market, which involves pacing of the left ventricle in conjunction with the right ventricle in an effort to "resynchronize" the heart, that is, to coordinate the left ventricle's contraction in time with the contraction of the right ventricle. One problem in the current therapy is the optimization of the placement of the left ventricular electrode so as to provide maximum therapy. Historically, an electrode may have been inserted into a site with the lowest activation threshold in order to maximize battery life. However, the optimal therapeutic site may not have the lowest activation, or stimulation, threshold.

This invention addresses this problem by providing intracardiac ultrasound imaging, ultrasound Doppler, and ultrasound speckle pattern tracking as new tools for the placement of the electrode and for the configuration of the pacemaker energizing it.

SUMMARY OF THE INVENTION

Various embodiments provide ultrasound image processing and analysis tools for assisting a clinician in diagnosing cardiac diseases and determining desirable sites for placement of a cardiac pacing electrode as well as determining how to configure the pacemaker which electrically drives the pacing electrode. Certain embodiments may measure, evaluate, compile, and compare the effectiveness of multiple combinations of specific electrode sites and specific pacemaker configuration settings. The embodiments may also compare those combinations with a measurement taken without the pacemaker active.

Desirable measurements for quantifying the effectiveness of a particular combination of electrode site and pacemaker configuration include estimating the volume of blood ejected from the heart during each cardiac cycle. The ejection volume may be expressed as an absolute volume or as a fraction relative to the maximum volume of the blood within a ventricle during the cardiac cycle. Ignoring all other factors, it is desirable for the ejection volume be maximized. Another useful measure can be the time or phase delay between the motions of the septal wall and the free wall of a ventricle during a cardiac cycle. Ignoring all other factors, it is desirable for this measure to be low. Further, ignoring all other factors, it is desirable to configure a pacemaker at the lowest reliable activation voltage in order to preserved battery charge. To facilitate comparison of the effectiveness of multiple electrode sites and pacemaker configurations when more than one measure is applied, it may be useful to use a single figure of merit value which is an evaluation function with all the applied measures as parameters.

Any such embodiment can include hardware and/or software, either on the ultrasound system, or on a separate system that directly or indirectly communicates with or receives data from the ultrasound system and a device that can digitize and/or transmit ECG data, if separate from the ultrasound unit. This device can utilize ultrasound data, in coordination with the ECG signals, to calculate the spacing between the walls of the left ventricle to estimate the maximum and minimum ventricular volumes and the relative motion of the ventricular walls in the course of a cardiac cycle.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain features of the invention.

FIG. 3 is an example of tabular data that an embodiment may display.

FIG. 5A illustrates a measurement technique for calculating cross-sectional area of the output from the ventricle.

FIG. 5B illustrates the basis of Doppler measurement used in an embodiment by delineating streamlined flow through a vessel, its profile through time and the basis of the time-integral area product showing volume of flow.

DETAILED DESCRIPTION OF THE PREFERRED EMBODIMENT

Figure 1:
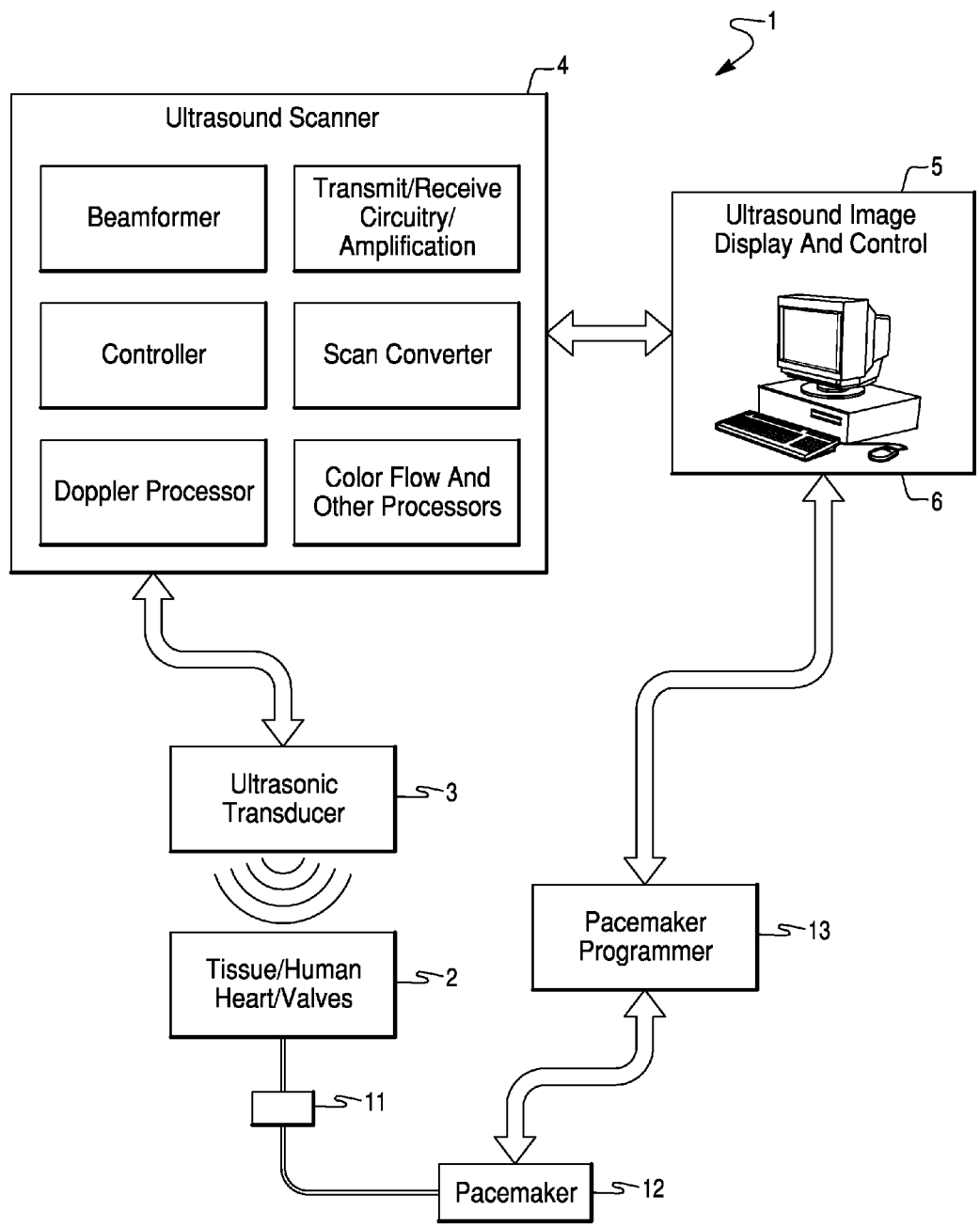
FIG. 1 provides a general system diagram showing an ultrasound system.

Heart failure is a disease where the heart's main function, a pump for blood, is wearing down. The heart tissue can absorb fluid, the left ventricle does not allow quick electrical conduction, becomes enlarged, does not contract well, and becomes less efficient at pumping blood. A measurement for the cardiac output (volume of ejected blood) is called the "ejection volume". The efficiency of the heart as a pump is called the "ejection fraction" or "EF". EF is measured as the percentage of the blood volume contained in a ventricle which is pumped out (ejected) with each beat of the heart. A healthy, young heart will have an EF greater than 90 (i.e., 90 percent of the ventricular blood is pumped with each heart beat); an older, sick heart in heart failure can have an EF less than 30 percent. Heart failure leads to an extremely diminished lifestyle, and, left untreated, can be a major cause of mortality.

A new therapy to treat heart failure is bi-ventricular pacing, or "resynchronization" therapy, where both ventricles of the heart are paced with an implantable pulse generator, commonly known as an artificial pacemaker. Normal pacing for a slow heart is performed via an implanted electrode in the right ventricle. The conduction myofibers (Purkinje fibers) conduct the electrical pulse and the ventricles contract synchronously in an inward direction, resulting in blood being pumped efficiently from the heart. In heart failure, the left ventricle becomes enlarged and conduction through the tissue of the left ventricular wall often becomes slow, so that the upper part of the left ventricle conducts as much as 200 to 250 milliseconds behind the apex area of the ventricles. This leads to poor and uncoordinated contraction, and in many cases, an outward movement of the heart muscle, so that blood sloshes around rather than being squeezed out of the ventricle. Thus, an ideal site to place a pacing electrode in the left ventricle is in the area of slowest conduction, which can be a rather large area of the left ventricle, and may not always be the area that has the largest conduction. The problem facing physicians today is to locate the optimal spot for the permanent fixation of the pacing electrode. The thrust of this invention is to provide a method and device to optimize the site of the electrode.

As used herein, the term "site" generally refers to a specific physical or anatomical feature or location on or within the heart, regardless of where location or feature moves spatially over time. The term "image location" generally refers to where an anatomical site is located within an ultrasound image at a specific time. An image location may be defined by 2-D pixel coordinates or by coordinates within an external frame of reference and the moment of time within a cardiac cycle. The term "3-D location" generally refers to where in a spatial coordinate system an anatomical site is located at a specific moment of time. A 3-D location may be located within a 3-D coordinate system (e.g., X,Y,Z) and the moment of time. The term "point" may be used interchangeably with "location". Nevertheless, the image location in a specific ultrasound image may correspond to a specific anatomical site, which in turn is located at a specific 3-D location at the moment corresponding to the image. Therefore, when describing a specific ultrasound image, the terms are often blurred, and a term sometimes may infer the physical site, the site's 3-D location at the moment of image capture, and/or the site's image location at the moment. The term "position" and its related forms usually include both the concept of a 3-D location and the concept of a 3-D orientation.

A standard pacemaker electrode is commonly implanted at a site in the cardiac wall which achieves the lowest activation "threshold." That is to say, the site for which the lowest voltage level is needed to excite the surrounding tissue to conduct synchronously the pacing signal from the electrode. Thus, in the past, the electrode has been implanted based upon merely finding the site where the lowest activation voltage is needed to stimulate the muscle tissue reliably. The rationale for this is to minimize battery drain. Placing the pacemaker electrode in the optimal site is not an easy task. Ideally, a site is chosen which optimizes the EF. Finding a site with a low threshold, while desirable, is not as important as optimizing EF. Thus, the ability to not only visualize the motion of the left ventricular wall, but also measure EF, or some form of output of the heart, such as stroke volume or flow rate, is highly desirable during the implantation procedure. The various embodiments use ultrasound technology to provide this ability.

The embodiments provide a toolset for using ultrasound imaging to evaluate and keep track of ventricular dyssynchrony or cardiac ejection volume for each of multiple combinations of electrode sites and pacemaker configurations. The measurements may be performed either automatically or with interaction from the attending physician, who may pre-specify certain operating parameters or measurement criteria. Measurements and the associated specific combinations of electrode sites and pacemaker configurations may be stored, retrieved, listed, ranked, or analyzed by the physician to judge which combinations may be optimal. Thus, the various embodiments described herein provide tools to assist a clinician in configuring a pacemaker and selecting an optimal site for the pacemaker electrode.

A diagram of an embodiment of the present invention is shown in FIG. 1. As shown in FIG. 1, an ultrasound imaging system 1 suitable for measuring cardiac output of a patient's heart 2 includes an ultrasound imaging transducer array 3. The ultrasound imaging transducer array 3 houses at least one ultrasonic transducer, which utilizes piezoelectric properties to generate acoustic signals from electrical signals in order to obtain ultrasound signals. The ultrasound transducer is of a type suitable for imaging the patient's heart and is used to obtain ultrasound signals associated with an area of the patent's heart in which cardiac output is to be measured. The transducer array 3 may be embedded within an intravascular catheter. The signals received from the ultrasound transducer array 3 are fed into an ultrasonic scanner unit 4 which contains the necessary digital or analog electronics to generate and process ultrasound signals from the at least one ultrasonic transducer array 3 to generate B-mode, M-mode, and/or Doppler representations of the patient's heart. These digital or analog electronics include, for example, a beamformer, transmit/receive circuitry and amplification circuitry, a controller unit, a scan converter, a Doppler processor, and color flow as well as other processors. In addition the system includes an associated ultrasound display and control console 5 that can generate and process the ultrasound signals in order to measure the cardiac output in the patient's heart and to measure the delay in the motion of a site on the cardiac wall with respect to the cardiac cycle.

The console 5 is configured to compute a measure of heart efficiency or functionality. The measure may comprise the cardiac ejection volume estimated from the ultrasound data for the specific combination of pacemaker configuration and electrode site. In addition to the ejection measurement, or instead of it, an embodiment may measure the dysynchrony delay between the motion of the septal and free walls of a ventricle, such as the left ventricle. An embodiment may employ any other measurement of cardiac output or some combination of measurements of cardiac functionality, which result from the combination of pacemaker configuration and choice of electrode site. If more than one electrode is present, then the term "electrode site" herein may refer to the sites of all the available electrodes.

Any method may be used for estimating ejection volume or ejection fraction using ultrasound. One exemplary method employs Doppler ultrasound signals or spectral Doppler signals. The Doppler signals, the boundaries of which can be either demarcated by the user, or automatically estimated by the system, along with the measure of the cross-sectional area through which such flow passes, which can again be either demarcated by the user, or automatically determined by the system, are utilized to calculate ejection volume of blood flow through the heart. For example, the ejection volume may be computed by integrating the average flow velocity over at least one cardiac cycle. Further, the average flow velocity at each moment may be assumed to be one-half of the peak velocity detected in the Doppler image taken at that moment, for example. That is, $$V_{ejt} = A \cdot \int (V_{peak}(t)/2)\, dt \qquad \text{Eq. 1a}$$

where: $V_{ejt}$=ejection volume;
A=cross sectional area of flow; and
$V_{peak}(t)$=peak velocity at time t in the cardiac cycle.

FIG. 5A is simplified drawing of an example spectral Doppler ultrasound image, which depicts the peak velocity over time during a cardiac cycle. FIG. 5B graphically illustrates the basis for this formula.

Figure 7A:
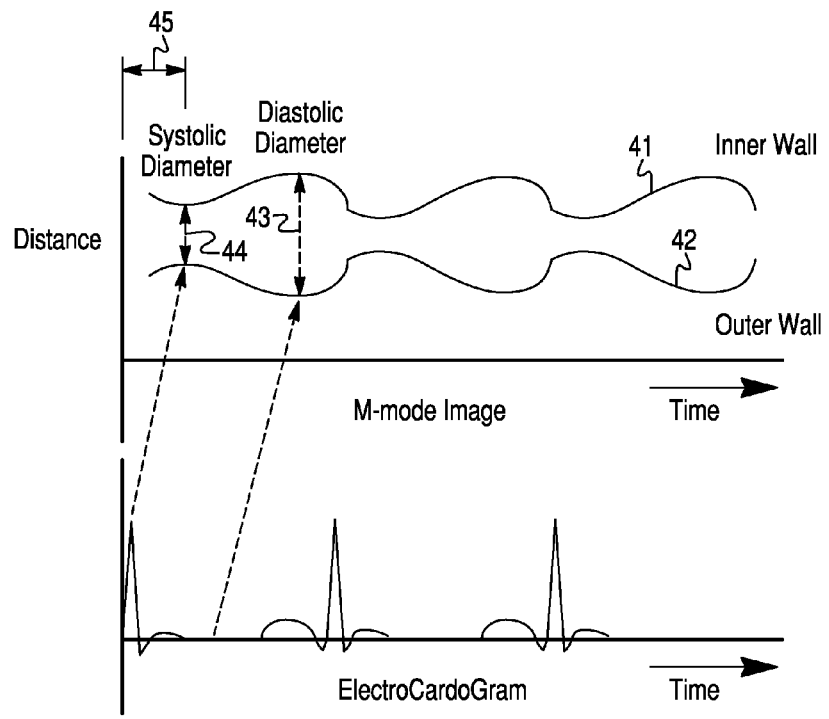
FIG. 7A-7C illustrate the basis of ejection volume measurements according to various embodiments.

An alternative computation for $V_{ejt}$ is provided by Eq. 1b, which is amenable to M-mode ultrasound images of the heart obtained at discrete imaging intervals Δt as illustrated in FIG. 7A. In this computation, dimensional measurements of the vessel diameter obtained from M-mode images are used to estimate ejection volume.

$$V_{ejt} = \sum_{t=0\ldots T} \pi R^2(t) L(t) \qquad \text{Eq. 1b}$$
$$= \sum_{t=0\ldots T} \pi R^2(t) v(t) \Delta t$$

where: $V_{ejt}$=ejection volume or stroke volume;
R(t)=one-half the distance between chamber walls in the M-mode image;
L(t)=v(t) Δt=flow distance during time Δt at time t; and
v(t)=mean flow velocity at time t.

Figure 7B:
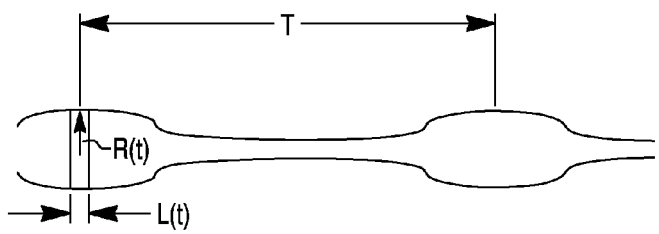

FIG. 7B illustrates the above computation graphically on a simplified rendering of an M-mode image. The value of R(t) may be measured manually on the ultrasound image display using calipers built into the M-mode ultrasound display or may be determined automatically using a computer graphics edge detection algorithm. As used herein, "calipers" refers to maximum and minimum measurements or threshold settings, which may be illustrated on a graphical display with horizontal indicators at the maximum and minimum levels or brackets. Using calipers, the maximum and minimum measured distance measurements or image locations of sites on the ventricle wall can be indicated with the upper and lower bounds of the caliper, so that the displacement distance is indicated by the separation between the end locations of the caliper. Because ultrasound can measure R(t) and dt accurately, the error in $V_{ejt}$ mainly depends on the accuracy of the measurement of v(t).

If the locations of a sufficient number of sites on the cardiac wall sites are determined and the sites are adequately distributed three-dimensionally, then a simple closed surface geometrical model may be constructed. The location coordinates of cardiac wall sites may be obtained, for example, from the image planes of multiple ultrasound transducer arrays or from a 3-D ultrasound system. The multiple transducer arrays may be intravascular, external to the heart, or both. If the 3-D coordinates of a dozen or so well distributed speckle points at a specific moment in the cardiac cycle can be measured thereby, for instance, a polyhedron, with those points as its vertices, can be constructed. Then the volume of the polyhedron would approximate the volume of the cardiac chamber, where the volume of the polyhedron is readily computed by known methods. Alternatively, a smoothly curved surface through the locations of cardiac wall sites (such as a NURBS surface) may be constructed using known computer graphics methods. Then the volume contained by that surface may be an even better approximation of the volume of the cardiac chamber. Approximating such a polyhedral or curved surface for 3-D locations measured at each of systole and diastole times in the cardiac cycle and calculating the difference between the volumes of those two surfaces may approximate the ejection volume.

In an embodiment which tracks the image coordinates of N wall sites of the ventricular cavity, the ejection fraction may be estimated by determining a best-fit affine linear transformation which maps the coordinates of the N sites at diastole to the coordinates of the same N sites at systole. The transformation may be two-dimensional if the N sites are all in one plane or may be three-dimensional if the N sites can be obtained in multiple planes. The best-fit linear transformation may be determined, for example, using the well-known least-squares method and may be represented by a homogeneous matrix M, as is common practice in computer graphics. Then for the three-dimensional case, the ejection fraction $F_{ejt}$ may be approximated as the square root of the product of the eigenvalues of $M^T M$. For the two-dimensional case, the ejection fraction $F_{ejt}$ may be approximated by the product of the eigenvalues of $M^T M$, assuming that the longitudinal dimension of the cardiac cavity remains fairly constant. N must be at least 3 for non-collinear sites in a plane. N must be at least 4 for non-coplanar sites. Smaller inaccuracy will generally result for larger values of N and for wall sites which are distributed around the cardiac chamber.

Figure 6:
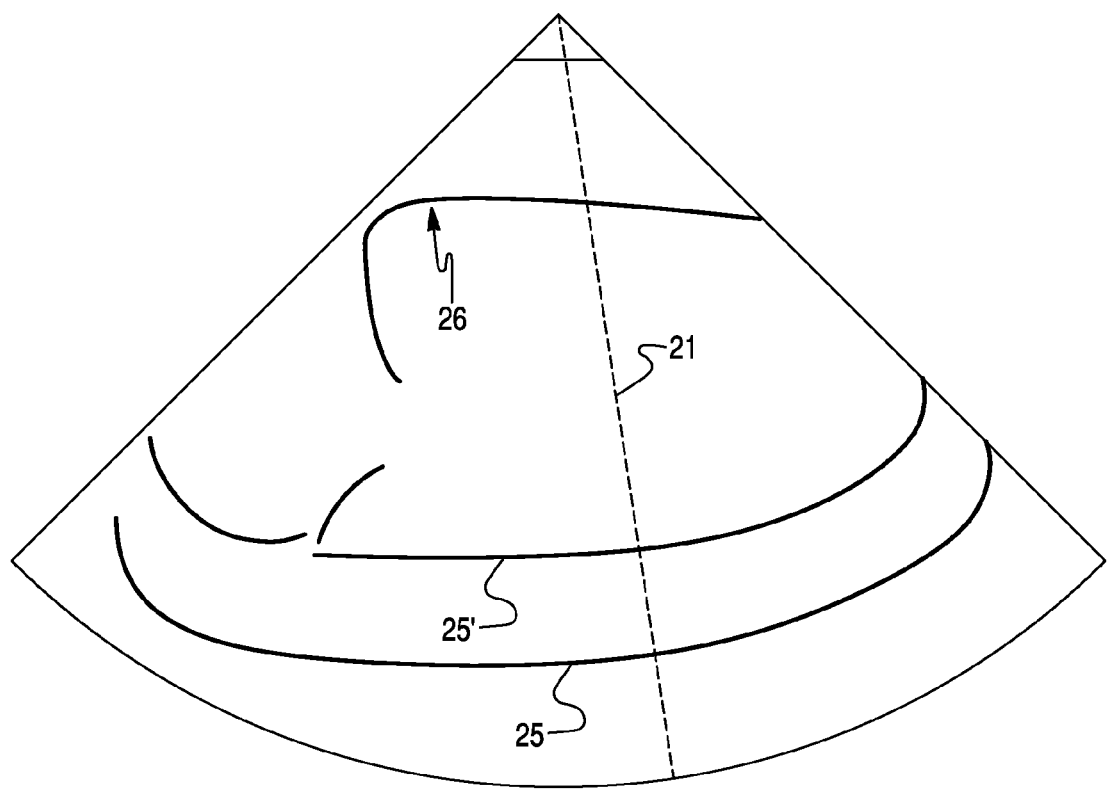
FIG. 6 illustrates a B-mode ultrasound image of a ventricle used in an embodiment.

Another example of a method for estimating ejection volume is to use an M-mode ultrasound image to measure the minimum (systolic) diameter $D_S$ and maximum (diastoic) diameter $D_D$ of a ventricle over the cardiac cycle. The EF can roughly be approximated by $$EF = (D_D^2 - D_S^2)/D_D^2$$

where: $D_D$=diastolic wall-to-wall diameter; and
$D_S$=systolic wall-to-wall diameter, assuming that a ventricular chamber length is approximately constant. FIG. 6 is a simplified drawing of a B-mode image with an M-mode cursor line. FIG. 7A provides a simplified example of an M-mode display corresponding to the cursor line of FIG. 6. FIG. 7A shows the diastolic wall-to-wall diameter 44 and systolic wall-to-wall diameter 43.

An example of a method for estimating dysynchrony delay within a ventricle also involves an M-mode display. Time axis calipers for the M-mode display can measure the time delay between the motion of two ventricular wall sites, one on the septal wall and one on the free wall. Another example, using an ultrasound B-mode display, is U.S. patent application Ser. No. 11/428,517, which is incorporated entirely herein by reference and which tracks the phased, regional motion of images of sites on the ventricular wall.

An embodiment which estimates the ejection volume or ejection fraction over a single cardiac cycle can be further enhanced by averaging the per-cycle stroke volume or the per-cycle ejection fraction over multiple cycles. Besides providing a more representative mean value, measurements over a number of cycles allows the computation of the statistical variation or standard deviation. The standard deviation then provides an indication of the "error", uncertainty, or untrustworthiness of the mean value.

Other systems and methods, such as speckle tracking methods, may be employed by the embodiments described herein to measure aspects of cardiac functionality or efficiency. U.S. patent application Ser. 11/610,888 entitled "Method And System For Estimating Cardiac Ejection Volume And Placing Pacemaker Electrodes Using Speckle Tracking", which is filed concurrently herewith and incorporated entirely herein by reference, describes such ultrasonic systems and methods for computing the cardiac ejection volume or ejection fraction and the cardiac dysynchrony between ventricular walls.

An embodiment includes a console 5 that may exist as part of the ultrasound scanner system 4. In such an embodiment, the system 4 may utilize the Doppler processing capabilities of the host ultrasound scanner to estimate the cardiac ejection volume. For example, the system may obtain a time-varying signal representative of the velocity of flow through a designated area of interest. Such area could include the inlet of the aorta from the left ventricle, or the valve in between. The system may then integrate the measured velocity of flow over the time of a cardiac cycle and integrate it across the area to compute the total ejection volume. The system may further express the total ejection volume as a fraction (percentage) of the maximum volume of the ventricular chamber from which the blood volume is ejected during a cardiac cycle.

As illustrated in FIG. 1, a clinician can use a pacemaker programmer 13 to set a pacemaker 12 to a specific configuration, such as setting the activation threshold voltage. In some situations, a clinician may use a pacemaker programmer 13 to program the pacemaker 12 manually, but in an embodiment, the clinician directs the pacemaker programmer 13 to configure the pacemaker 12 by entering settings and commands into a computer 6 connected through an electronic interface to the pacemaker programmer 13. Among other possible configuration parameters, the activation voltage of the pacemaker 12 may be set by the pacemaker programmer 13.

A cardiac pacing electrode 11 driven by the pacemaker 12 is positioned by the clinician at a specific site on the patient's heart 2, and the pacemaker 12 is placed into operation. During the electrode emplacement and pacemaker programming procedure, the heart 2 is imaged by the intracardiac ultrasound transducer 3 coupled to the ultrasound imaging system 4.

Figure 2A:
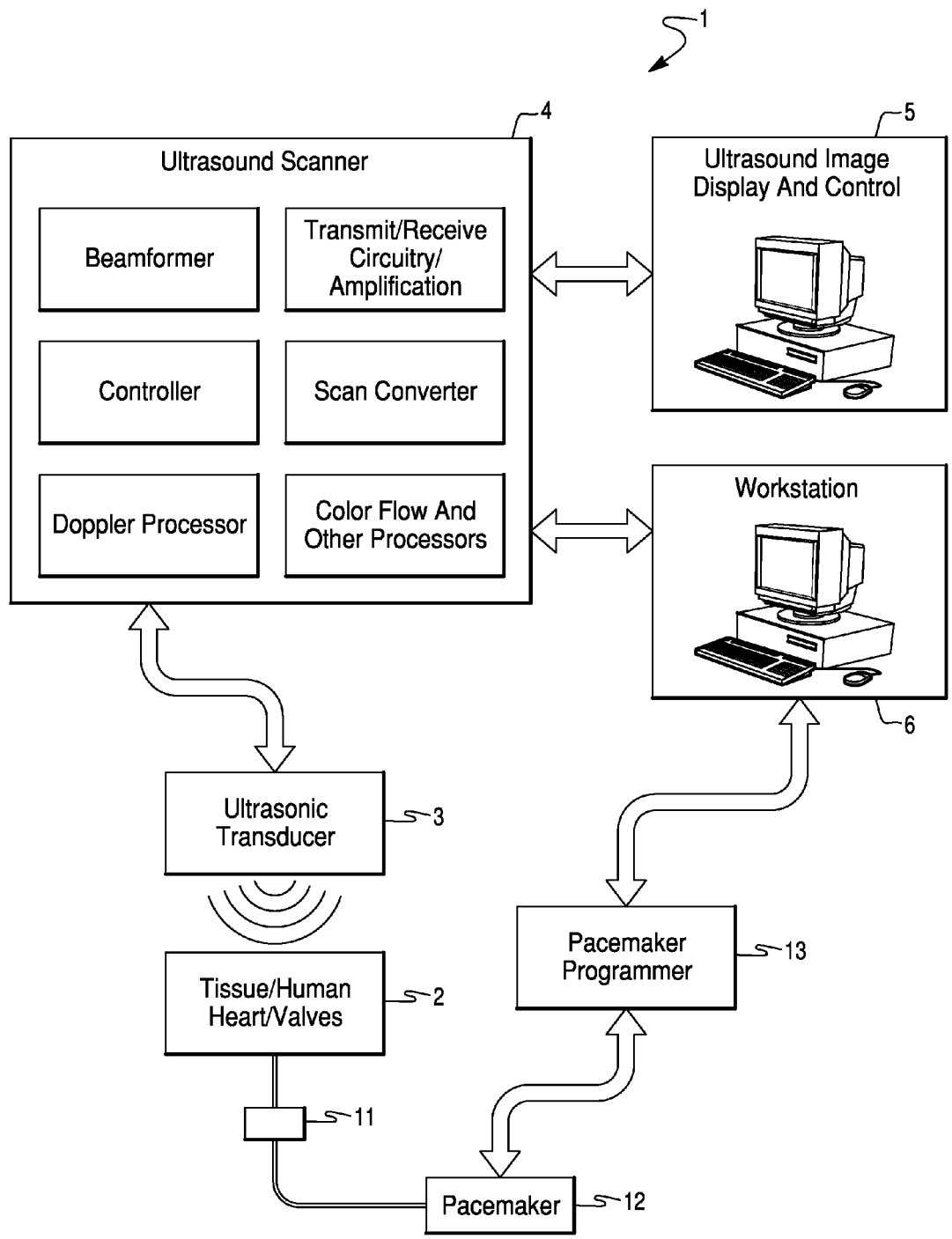
FIGS. 2A, 2B, and 2C illustrate various embodiments of the present system with an attached workstation.
Figure 2B:
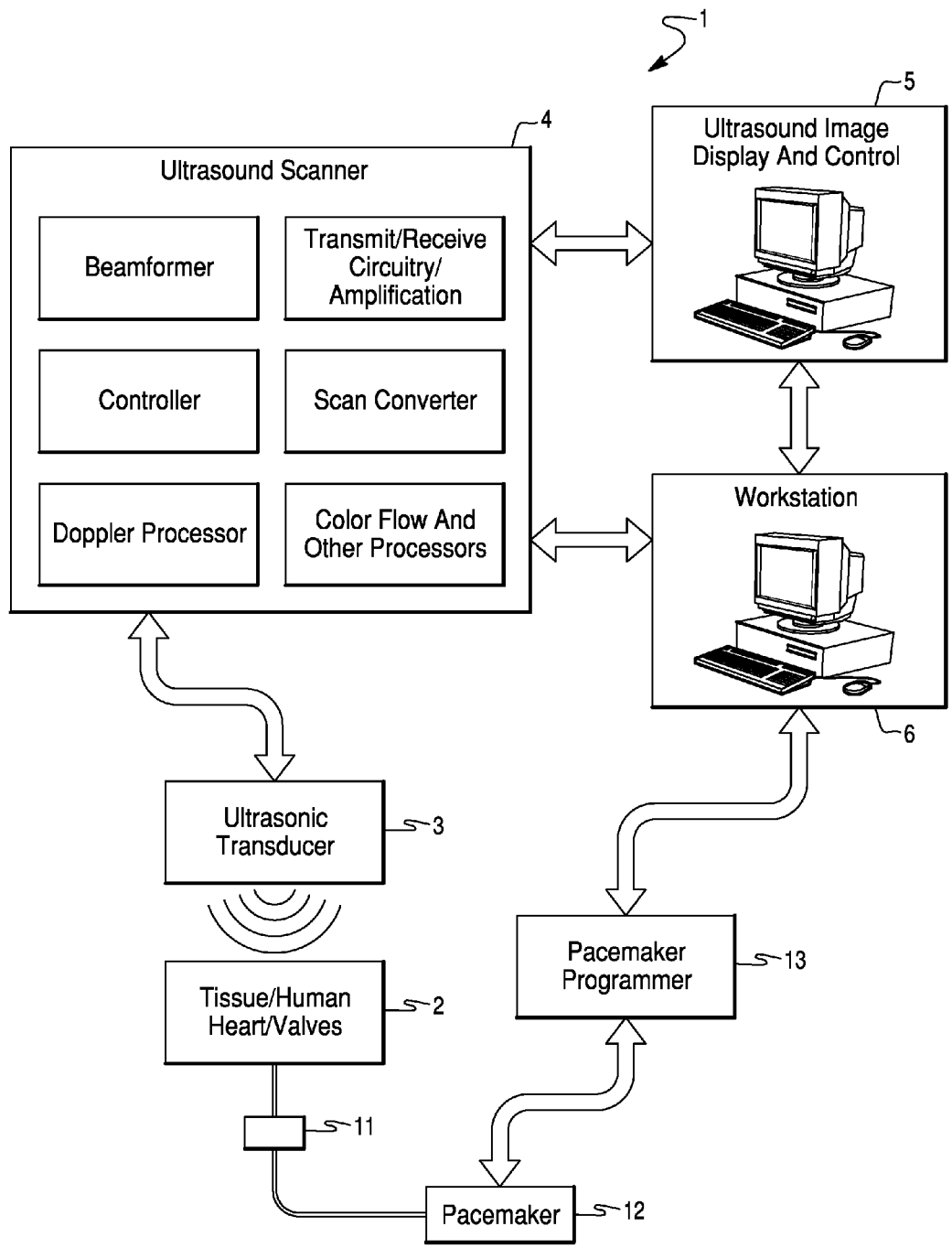
Figure 2C:
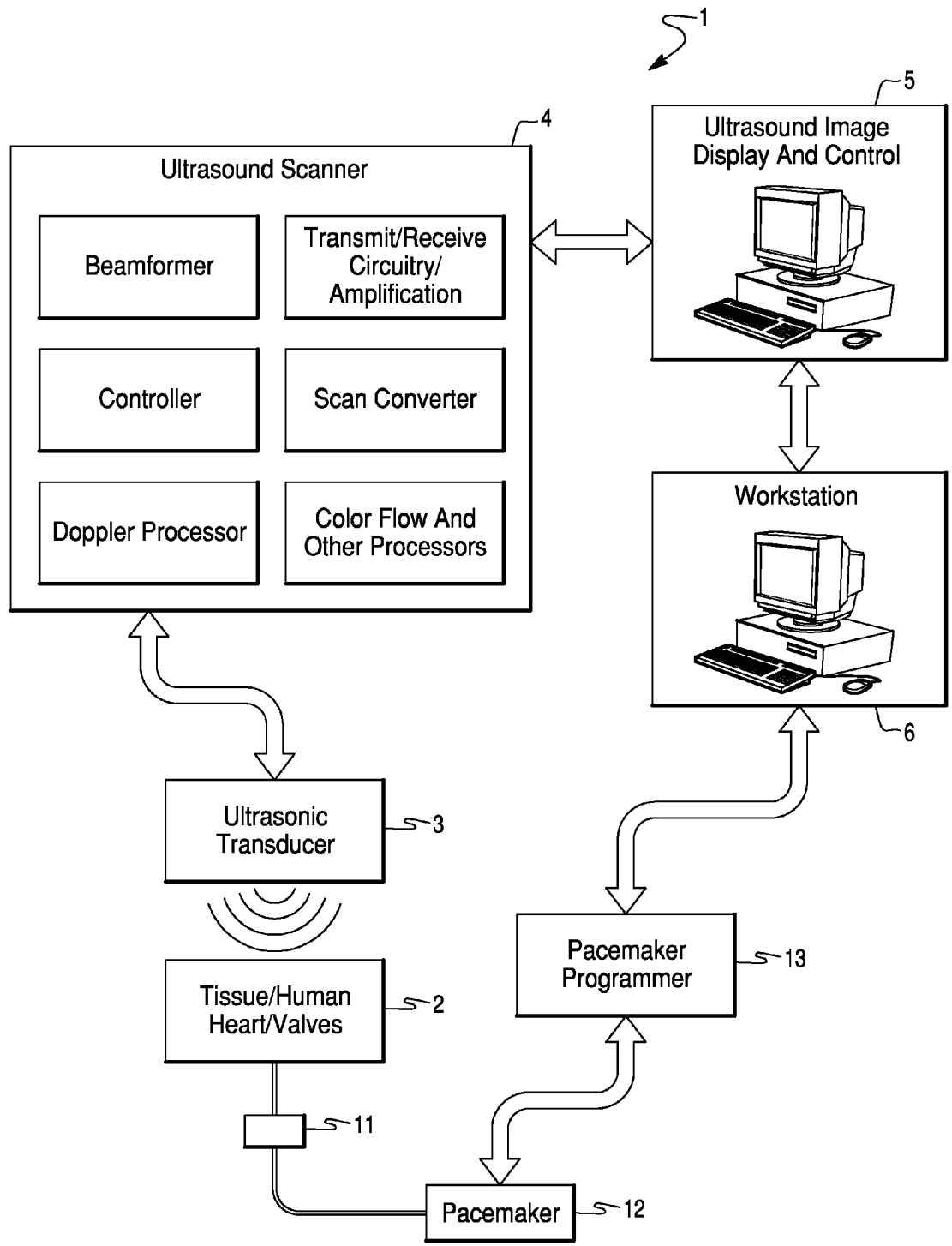

Other embodiments of the present invention are in the form of computer hardware 6, and software executing on it, which exists separate from the ultrasound scanner console 5 or the ultrasound system 4. Such embodiments may use cable or wireless circuits to communicate between the ultrasound scanner 4 and the separate computer 6 and/or between the ultrasound console 5 and the separate computer 6. Example block diagrams of such embodiments are shown in FIGS. 2A, 2B, and 2C. Communication between or among the separate computer 6, the ultrasound console 5, and the ultrasound scanner 4 can include processed ultrasound data, as well as video, audio, and/or any ECG signals in digital and/or analog format. The processing described herein can then be performed either partially or entirely on the separate computer 6 executing software instructions implementing the methods.

An embodiment combines the functionality of the separate computer 6 with the ultrasound console 5 into one hybrid unit, as shown in FIG. 1. This embodiment may also combine the software executing on computer 6 with the software executing on ultrasound console 5. Further, in alternative embodiments, steps of the various method embodiments described herein as being performed on the computer 6 may be performed on the ultrasound console 5, and steps described herein as being performed on the ultrasound console 5 may alternatively be performed on the computer 6. For simplified discussion, this specification treats the computer 6 of FIGS. 2A-2C as at least functionally, if not physically, separate from the ultrasound console 5. That is, for simplified discussion, various cardiac measurements derived from the ultrasound images will be described as being performed on the ultrasound console 5. Further processing based on those measurements will be described as being performed on the computer 6, which may include saving, retrieving, and evaluating combinations of pacemaker configurations and electrode sites. However, such descriptions are not intended to imply or require that different functionalities are performed by separate physical processors, and can be performed by the same processor in some embodiments.

In an embodiment, the computer 6 saves in memory at least one measurement of cardiac efficiency along with data concerning the corresponding combination of pacemaker configuration and the electrode site which produced the measurement or measurements. The configuration, the electrode site, and measurement information to be saved in memory may be acquired automatically, obtained semi-automatically, or entered manually by the clinician. An embodiment further may retrieve from memory the measurement, the pacemaker configuration, and the electrode site of any of the saved combinations which have been tried. An embodiment can provide a display of the saved information summarizing some or all of the tried and saved combinations and the corresponding cardiac efficiency measurements. Still further, the saved information may optionally be ranked or displayed according to at least one criterion. For example, the saved information may be ranked and listed (1) in decreasing order of the amount of ejection fraction, (2) in increasing order of the activation voltage, (3) in increasing order of the least average septal-to-free-wall delay, or (4) a combinatorial blend of those values. An embodiment may allow the ranking or display criterion to be specified by the clinician. An embodiment may allow a user to delete saved information that is no longer of interest, such as one or more of the lower ranked combinations.

An embodiment may save or display the site of the pacing electrode in any form helpful to the clinician. Suitable forms include textual descriptions and graphical images. A nonlimiting example of such a display includes one or more ultrasound images on which the image locations of electrode sites are indicated with representative labels, icons or color-coded markers. Another example embodiment may show a hybrid form, such as numerical data together with a connector or pointer on the image pointing to the corresponding image location of the site of the electrode on a saved ultrasound image. FIG. 3 is an example for illustration purposes only of a tabular display of the information saved for several combinations of electrode site and activation voltage. In the example shown in FIG. 3, each site is simply referenced by a letter, where the letter also appears on a display of a corresponding saved image or images of the heart at the location of the electrode corresponding to the numerical data. The example in FIG. 3 also includes the cardiac measurements corresponding to the heart without pacemaker activation.

In an embodiment, such as the example illustrated by FIG. 1, an electrode 11 is positioned at a specific endocardial or epicardial site and is activated by a pacemaker 12 having a specific configuration. Various embodiments assist a clinician in finding an optimal site and configuration that will reduce dysynchrony (time lag between the motion of the septal wall and the motion of the free wall) and/or increase cardiac ejection volume. At the same time, it may be desirable to configure the pacemaker, for example, with the lowest reliable activation voltage to conserve battery life. Because dysynchrony, ejection volume, and activation voltage interact and do not necessarily correlate, a figure-of-merit evaluation function having such multiple factors as variables is desirable. The figure-of-merit evaluation function's coefficients reflect the relative importance of each variable and can be tailored to various patient circumstances and conditions.

A nonlimiting example of a mathematical function F which assigns a figure-of-merit to the multiple cardiac measurements is the following:

$$F(E,D,V) = C_E \cdot E - C_D \cdot D - C_V \cdot V$$

where:
   $C_E$, $C_D$, and $C_V$ are non-negative coefficients;
   E is the ejection fraction or is ejection volume (which is desirably high);
   D is the dysynchrony delay time or phase (which is desirably low); and
   V is the activation voltage (which is desirably low).
   The values of the coefficients $C_E$, $C_D$, and $C_V$ may be determined from clinical experience and may depend on the age and health of the patient or on other factors. Assuming that larger values of function F signify more desirable combinations of E, D, and V, the value of function F should increase as the ejection fraction (or ejection volume) E increases. The value of function F should decrease as the dysynchrony delay D decreases, where D may be a time lag in milliseconds. The activation voltage V may be less important, but normally should be low, if ejection volume and dysynchrony are reliably maintained. That is, F should increase as V decreases. The evaluation function F yields a single figure of merit which relates the variables. The relative magnitudes of the coefficients reflect the relative importance of each argument E, D, and V. An embodiment allows a clinician to optionally change the values of the coefficients based on personal experience, on the characteristics of the cardiac patient or intended clinical use for the figure-of-merit.

To optimize the figure-of-merit, if used, or to optimize any chosen single measurement of cardiac functionality, the clinician can repeatedly try attaching the electrode at various sites and try using various pacemaker configurations. Each new proposed combination may be based on previously measured dysynchrony, ejection volume or fraction, electrical activity, or other measurements. The clinician can use the figure-of-merit, or any chosen single measurement, to confirm or select one choice from the various combinations. Further, the clinician may use the figure-of-merit to compare the various tried combinations with a baseline figure-of-merit. The baseline figure-of-merit is computed from a measurement or measurements of cardiac functionality measured when the pacemaker is electrically inactive or when there is no electrode at a site. Such a baseline measurement may be taken before, between, or after the measurements are taken for which an electrode at a cardiac site is active.

Therefore, when comparing two (or more) configurations using a figure-of-merit computed using function F, as defined above, the configuration exhibiting the highest value is most desirable. This is because the higher figure-of-merit is likely to reflect an optimal electrode site and/or configuration for a pacemaker. The figure-of-merit value computed from saved measurement information may be displayed along with the saved measurements, electrode sites, and pacemaker configurations in order to reveal which configuration will provide the best therapeutic result. The value of the figure-of-merit may be displayed numerically, graphically, as a color code representing the value, or as some combination thereof. Function F is unnecessary if only a single measure of cardiac functionality is consistently utilized to judge the optimal electrode site.

Alternatively, the figure-of-merit function may be defined so that the optimal values of its independent variables produce a minimum resultant value of the function instead of a maximum value. Therefore, the description of various embodiments may use the term "optimal figure-of-merit value" for either a minimal value or maximal value, as appropriate, which corresponds to an optimal combination of electrode site, pacemaker setting and other configuration variables.

An embodiment provides permanent data storage for archiving one or more of the saved evaluated combinations of electrode site and pacemaker configurations along with the corresponding cardiac efficiency measurements and figures-of-merit. Such storage may be a printed hardcopy or may be electronic data stored on a magnetic, electronic, or optical storage medium The computed figure-of-merit for the measurements corresponding to a specific site-configuration combination may be saved with the combination and measurement information. Alternatively, or the figure-of-merit may be dynamically recalculated each time its value must be displayed using stored factor data. Dynamic recalculation can allow all the figures-of-merit values to be updated immediately after a new figure-of-merit function is been defined or adjusted.

Figure 4:
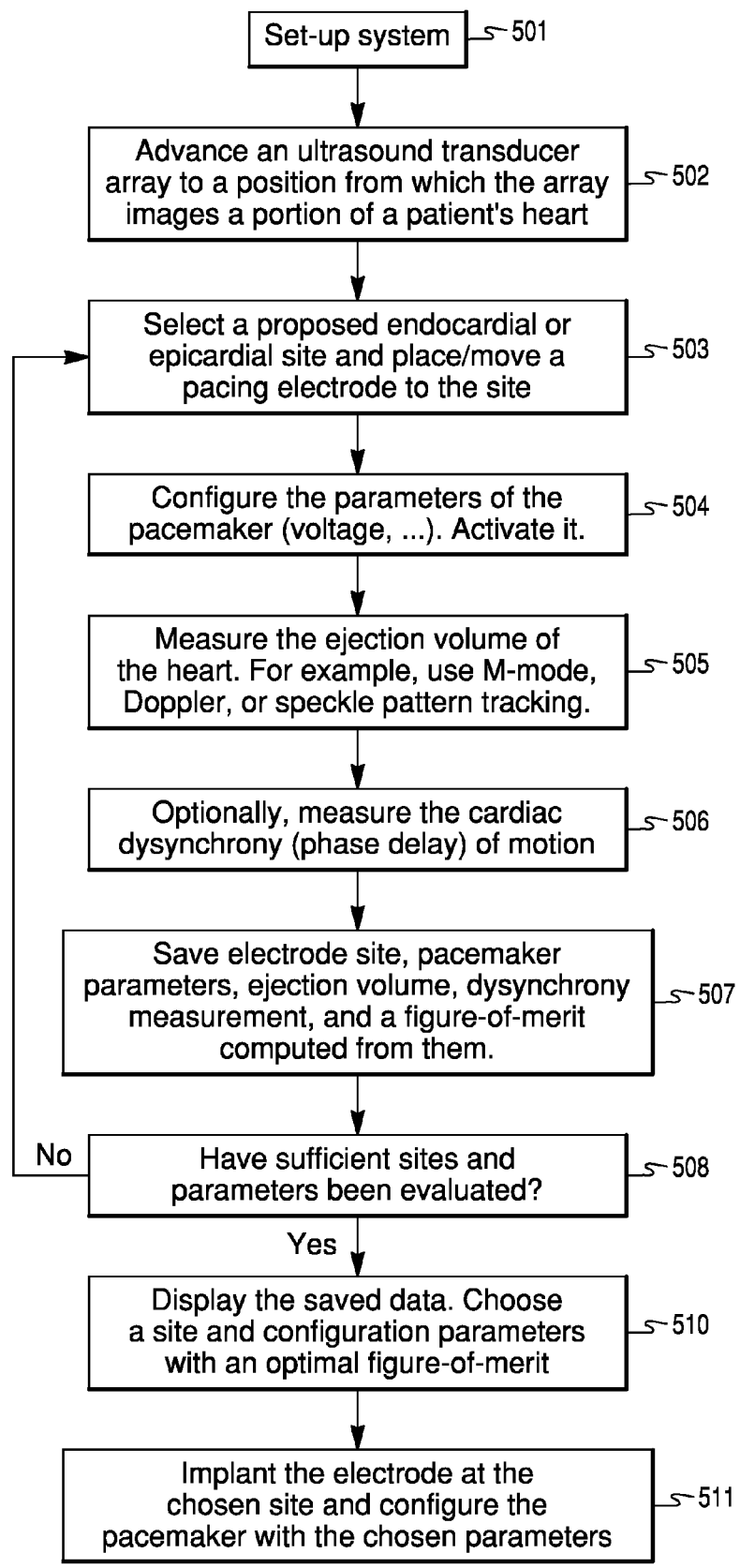
FIG. 4 provides a flowchart illustrating a procedure for determining a potential site for a pacemaker electrode implant and determining a configuration for the pacemaker.

The flowchart of FIG. 4 provides an embodiment of a method for aiding a clinician in determining a potential optimal site for a pacemaker electrode and an optimal configuration for the pacemaker. The clinician sets up and initializes the equipment, step 501. The clinician positions a cardiac catheter, which includes an imaging ultrasound transducer array, so that the transducer array in conjunction with an ultrasound scanner unit yields an image of a portion of the patient's heart, step 502.

The clinician selects a site on the heart (such as on the free wall of the left ventricle) and places a pacemaker or stimulator electrode at that site, step 503. The clinician configures the pacemaker or stimulator to which the electrode is connected, step 504. The configuration parameters include at least the activation voltage level, but may contain other parameters relating to the activation pulse, such as the pulse shape or duration, the activation pulse frequency, and so forth. The configured pacemaker or stimulator is placed into active operation using the located electrode. Any one or more known ultrasound techniques are used for estimating the ejection volume or ejection fraction, step 505. The cardiac dysynchrony (time or phase delay between motions of the ventricular walls) is measured relative to the cardiac cycle in addition to or instead of the ejection volume, step 506. A reference cardiac cycle may be defined by an ECG signal (if available) or by the motion of a reference site on the cardiac wall.

Figure 7C:
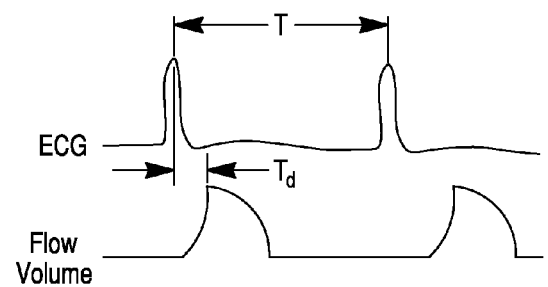

Further, an embodiment may provide a manual control or an automated detection of the delay $T_d$ between the ECG R wave and the maximum measured ventricular volume, and possibly also the delay between the ECG R wave and the minimum ventricular volume. This may be of particular significance for pacemaker configuration and electrode placement. This delay is illustrated in FIG. 7C.

The computer saves an indication of the electrode site, the pacemaker configuration parameters, the ejection volume (or ejection fraction), the dysynchrony measurement, or other measures of cardiac efficiency, step 507. As a function of the saved information, the computer may also compute a figure-of-merit associated with the saved information, step 507. The figure-of-merit is used or is applied to evaluate the degree of effectiveness provided by the pacemaker configuration and the electrode placement. The figure-of-merit may be saved with the other saved information, or it may be dynamically recomputed as needed. (An example of a possible mathematical function for computing a figure of merit is provided herein.) The clinician may then move the electrode to another position on the heart and/or adjust the pacemaker or stimulator settings. The other electrode sites and/or other pacemaker/stimulator configurations may be evaluated by computing the figure-of-merit for those sites and those configurations, step 508. This adjusting and evaluating continues until the clinician acquires sufficient information to make an evaluation.

When the clinician determines that enough information has been acquired, the computer displays the information in a graphical or tabular form, step 510. The clinician then chooses a combination of an electrode site and a pacemaker configuration, presumably one which is associated with an optimal figure-of-merit, step 510. The clinician can then implant the electrode at the chosen site and program the pacemaker to use the chosen configuration, step 511.

The various steps of FIG. 4 may be executed manually such as by a clinician, semi-automatically such as by a clinician assisted by a computer, or automatically such as by a computer. FIG. 4 lists the steps of an embodiment in a specific order. Nevertheless, the steps need not be necessarily executed in the order described above and shown in FIG. 4. For example, either the choosing of an electrode site or the programming of the pacemaker for activating the electrode at that site may be performed before the other, or they may be performed in parallel. Further, the measurement of the ejection volume, the measurement of dysynchrony, or any other such measurements may be performed in any order, simultaneously, or in any combination. Further, the figure-of-merit need not be computed until all the trial site-configuration combinations have been measured, saved, and listed. In yet a further step, baseline measurements may be taken when no electrode is embedded in the heart or no voltage is applied to an electrode, and the figure-of-merit may be applied also to those measurements. The baseline measurements may be acquired before or after or between measurements taken with an active electrode.

In FIG. 4, step 510 may further comprise steps of ranking the saved site-configuration combinations and the associated measurements, deleting those not of interest, evaluating the saved combinations with the figure-of-merit function, redefining the figure-of-merit function and re-evaluating the combinations using it, printing the saved combinations and measurements, and archiving the saved combinations and measurements.

If more than one electrode is being implanted, the above procedure is usable with the addition that the sites of all electrodes can be saved as one "site-assemblage" instead of a simple single site. Moving just one electrode of the assemblage to a new site may constitute a new "site-assemblage".

Of course, various combinations and/or modifications of these techniques and systems can be used if desired and depending on the particular application and/or patient.

Additionally, imaging and site motion tracking according to various embodiments may be used to image an unsteady pacing area or electrically malfunctioning area within the heart detected or located using ECG sensor data. For example, U.S. Patent Provisional Application No. 60/795,912, entitled "Method For Simultaneous Bi-Atrial Mapping Of Atrial Fibrillation" which is incorporated herein by reference in its entirety, describes methods for locating malfunctioning areas of the heart using ECG data mapped on an anatomical model of the heart. By using the various embodiments to track or image the unsteady pace or otherwise malfunctioning region in the conductive pathway, the resulting site tracking or images may enable the physician to more accurately locate and optimize the positions for pacing leads. Further, motion tracking of the selected region may enable the physician to more accurately optimize the pacing timing and rhythm for the lead, both by measuring the lag before emplacement to estimate an appropriate timing parameter and by measuring the lag after pacing is initiated to confirm the region is responding as desired to the pacing stimulation. Additionally, site tracking and ultrasound images of the heart may be used to correct, correlate or otherwise improve the anatomical model used for displaying ECG data In a further embodiment, the ultrasound system, isolation box and temperature monitoring/cutoff circuits may be packaged as a combined unit which can be placed close to the patient and eliminate or shorten some of the cables required for a system comprised of separate components.

It is to be understood, however, that even though numerous characteristics and advantages of the present invention have been set forth in the foregoing description, along with details of the structure and function of the invention, the disclosure is only for illustrative purposes. Changes may be made in detail, especially in matters of shape, size, arrangement, storage/communication formats and the order of method steps within the principles of the invention to the full extent indicated by the broad general meaning of the terms in which the appended claims are expressed.

What is claimed is:

1. A cardiac ultrasound imaging system for helping a clinician select a pacemaker electrode site and configure a pacemaker, the system comprising:

an intracardiac ultrasound imaging system configured to image a patient's heart; and a computer configured to:

process images generated by the ultrasound system in order to compute a measurement of cardiac ejection volume for a given pacemaker configuration and electrode site;

save two or more combinations of the corresponding pacemaker configuration, the corresponding electrode site, and the ejection volume measurement;

save a cardiac dysynchrony measurement and an activation voltage for each of the saved combinations;

retrieve the ejection volume measurement, the pacemaker configuration, and the electrode site of any of the save combinations; and determine a figure-of-merit value for each saved combination by applying a function comprising:

$$F(E,D,V) = C_E \cdot E - C_D \cdot D - C_V \cdot V$$

wherein:

$C_E$, $C_D$, and $C_V$ are non-negative coefficients;

E is the saved cardiac ejection volume or ejection fraction computed relative to a maximum cardiac volume;

D is dysynchrony delay time or phase obtained from the saved cardiac dysynchrony measurement; and V is the saved activation voltage; and wherein the computer is configured to display a saved combination in conjunction with the determined figure-of-merit value for each of the saved combinations.

2. The system of claim 1, wherein the computer is configured to display at least one of the saved combinations.

3. The system of claim 1, wherein the computer is configured to rank the saved combinations according to a specified criterion.

4. The system of claim 3, wherein the criterion is activation voltage and the combinations are ranked in order from lowest voltage to highest voltage.

5. The system of claim 3, wherein the criterion is ejection volume and the combinations are ranked in order from most volume to least volume.

6. The system of claim 3, wherein the criterion is dysynchrony timing delay and the combinations are ranked in order from least delay to most delay.

7. The system of claim 3, wherein the computer is configured to accept the criterion as an input provided by a user of the system.

8. The system of claim 1, wherein the computer is configured to associate the electrode site of a saved combination with a site on an image of the heart.

9. The system of claim 1, wherein the computer is configured to rank the saved combinations in order according to the figure-of-merit value.

10. The system of claim 1, wherein the computer is configured to accept the function coefficients from a user of the system.

11. A method for helping a clinician to select a pacemaker electrode site and to configure a pacemaker, the method comprising:

positioning a pacemaker electrode at a site on a patient's heart;

configuring the pacemaker with operational parameters;

imagining the patient's heart with an intracardiac ultrasound imaging system;

computing a measure of cardiac ejection volume;

saving in a computer memory a combination of the measure of cardiac ejection volume, the corresponding pacemaker operational parameters including an activation voltage, a dysynchrony measurement, and the corresponding electrode site;

performing the positioning, configuring, imaging, computing, and saving steps for two or more different combinations of electrode site and pacemaker operational parameters;

retrieving from the computer memory the saved measure of cardiac ejection volume, the pacemaker operational parameters, and electrode site of at least one of the saved combinations; and applying a function to each saved combination to return a figure-of-merit value for the combination, the function returning the figure-of-merit value comprising applying the formula:

$$F(E,D,V) = C_E \cdot E - C_D \cdot D - C_V \cdot V$$

wherein:

$C_E$, $C_D$, and $C_V$ are non-negative coefficients;

E is the saved cardiac ejection volume or ejection fraction computed relative to a maximum cardiac volume;

D is dysynchrony delay time or phase obtained from the saved cardiac dysynchrony measurement; and V is the saved activation voltage; and displaying at least one of the saved combinations in conjunction with the determined figure-of-merit value for the at least one of the saved combinations.

12. The method of claim 11, further comprising displaying at least one of the saved combinations.

13. The method of claim 11, further comprising ranking the saved combinations according to a criterion.

14. The method of claim 13, wherein the criterion is activation voltage and said ranking comprises ranking the saved combinations in order from lowest voltage to highest voltage.

15. The method of claim 13, wherein the criterion is ejection volume and said ranking comprises ranking the saved combinations in order from most volume to least volume.

16. The method of claim 13, wherein the criterion is dysynchrony timing delay and said ranking comprises ranking the saved combinations in order from least delay to most delay.

17. The method of claim 13, further comprising a user of the method specifying the criterion.

18. The method of claim 11, further comprising associating the electrode site of a saved combination with a site on an image of the heart.

19. The method of claim 11, wherein the ranking is performed according to the figure-of-merit value.

20. The method of claim 11, further comprising saving a baseline combination of the ejection volume measured without stimulation of the patient's heart.

21. The method of claim 11, further comprising saving notes, markers, and annotations with the saved site, configuration, and measurements.

* * * * *